US006555145B1

(12) United States Patent
Cherukuri

(10) Patent No.: US 6,555,145 B1
(45) Date of Patent: Apr. 29, 2003

(54) ALTERNATE ENCAPSULATION PROCESS AND PRODUCTS PRODUCED THEREFROM

(75) Inventor: Subraman Rao Cherukuri, Vienna, VA (US)

(73) Assignee: Capricorn Pharma, Inc., Frederick, MD (US)

( * ) Notice: Subject to any disclaimer, the term of this patent is extended or adjusted under 35 U.S.C. 154(b) by 0 days.

(21) Appl. No.: 09/587,971

(22) Filed: Jun. 6, 2000

(51) Int. Cl.[7] .................. A23L 1/025; A23L 1/304; A23L 2/56; A23L 2/60
(52) U.S. Cl. .................. 426/3; 426/4; 426/72; 426/73; 426/103; 426/638; 426/650; 426/660; 524/777; 524/947; 524/948; 524/951; 524/959; 424/405; 424/409; 424/439; 424/440; 424/463; 424/474
(58) Field of Search .................. 426/4, 103, 72, 426/74, 650, 660, 638, 3; 424/463, 408, 409, 439, 440, 474; 514/777, 947, 948, 951, 959

(56) References Cited

U.S. PATENT DOCUMENTS

| 4,568,560 A | 2/1986 | Schobel |
| 4,740,376 A | 4/1988 | Yang |
| 4,975,270 A | 12/1990 | Kehoe |
| 4,981,698 A | 1/1991 | Cherukuri et al. |
| 5,004,595 A | 4/1991 | Cherukuri et al. |
| 5,266,335 A | 11/1993 | Cherukuri et al. |
| 5,660,860 A * | 8/1997 | Fielden ................ 424/464 |

FOREIGN PATENT DOCUMENTS

| EP | 0 273 001 | 6/1988 |

* cited by examiner

*Primary Examiner*—Helen Pratt
(74) *Attorney, Agent, or Firm*—Nath & Associates PLLC; Gary M. Nath; Jerald L. Meyer

(57) ABSTRACT

A novel encapsulated product is provided and includes: at least one active ingredient; at least one compressible material; and at least one tableting material; wherein the encapsulated product is in the form of a caplet having a diameter of from about 1 millimeter to about 7 millimeters and a length from about 1 millimeter to about 7 millimeters. A method for preparing the encapsulated product is also provided. The encapsulated product may be incorporated into a food item, a confectionery product or chewing gum product.

21 Claims, No Drawings

ALTERNATE ENCAPSULATION PROCESS AND PRODUCTS PRODUCED THEREFROM

BACKGROUND OF THE INVENTION

1. Field of the Invention

The present invention relates to an alternate encapsulation process, and in particular, an alternate encapsulation process for concentrating additives using compression.

2. Description of the Prior Art

Various types of chewable articles are known in commerce. These articles include food items such as food items, confectionery items and chewing gum. The chewable articles often include various types of active agents or ingredients within the chewable articles. Examples of such active ingredients include flavors, sweeteners, colors, medicaments, vitamins, minerals, and other effervescent agents.

It has been known in the art of food stuff, confectionery and chewing gum preparation to provide protection to the active ingredients by the use of protection systems, including providing a protective coating around the active ingredient or encapsulating the active ingredient. Such protective systems have been employed for various reasons, such as for protection of the active ingredient, both while on the shelf and during use, and for prolonged release in the oral cavity.

It is known in the art to protect active ingredients by encapsulating the active ingredient prior to introducing the ingredient into a final product. Some of the major classifications of encapsulation technology include liquid suspending media (water-in-oil emulsions and oil-in-water emulsions), interfacial and in situ polymerization, solvent evaporation from emulsions, desolvation, complex coacervation, polymer and polymer incompatibility, gelation, and pressure extrusion. One of skill in the art will be familiar with each of these classifications.

Schobel, U.S. Pat. No. 4,568,560, discloses encapsulated fragrances and flavors for use in denture cleanser compositions. Schobel discloses encapsulating a solid particulate flavoring agent or fragrance with a film of an acrylic polymer and ethylcellulose. The encapsulation is accomplished utilizing a fluidized bed of the flavoring agent or fragrance.

Yang, U.S. Pat. No. 4,740,376, discloses encapsulating an active ingredient in a solvent free encapsulation composition which includes a blend of a high molecular weight polyvinyl acetate and a hydrophilic plasticizer. The active ingredient is protected from deterioration due to moisture and is provided with controlled release for use in a product to be ingested by a mammal.

Cherukuri et al., U.S. Pat. No. 4,981,698, discloses a delivery system for sweeteners that comprises a first high intensity sweetener encapsulated in a first core coating, and a second outer hydrophilic coating containing up to the solubility limit of the second coating of a second sweetener. The delivery system offers enhanced up front sweetness intensity in combination with prolonged sweetness duration, and improved protection and stability of the sweetener.

Cherukuri et al., U.S. Pat. No. 5,004,595, discloses a free-flowing particulate delivery system for providing enhanced flavor and sweetness to comestible products. The delivery system includes an encapsulating matrix that protects flavor in a core.

Cherukuri et al., U.S. Pat. No. 5,266,335, discloses microencapsulated flavoring agents and methods for preparing the same. The microencapsule comprises a flavoring agent and a resin in the core, and a coating layer over the core. The core is encapsulated by emulsion of a flavoring agent and a resin with a coating layer prepared by complex coacervation of a mixture of two or more colloidal materials.

Kehoe, U.S. Pat. No. 4,975,270, discloses elastomer encased active ingredients. The active ingredients are physically encased in non-porous, chewable particles of elastomer. The particles are then incorporated into articles of commerce.

There are a number of disadvantages when using the traditional encapsulation processes to encapsulate active ingredients. The disadvantages include the need for heat and moisture in order to properly form the encapsulated final product. Also, most encapsulation methods are complex and consume large amounts of time in order to obtain the final encapsulated product. Further, current encapsulated ingredients vary in size from nanometers to about 400 microns, and the active ingredients are not uniformly distributed throughout the encapsulated product.

A further problem is encountered when the active ingredients are vitamins and minerals. It is difficult to add both vitamins and minerals to a confectionery or chewing gum product because, in general, vitamins are many times incompatible with minerals when attempting to add both to a comestible product.

Therefore, there remains a need for an alternate encapsulation method for providing a product with high levels of active ingredients and in which water is not needed during the encapsulation process, nor is heat an essential feature of the encapsulation process. There also remains a need for an alternate encapsulation method which produces capsules with uniform active ingredient content throughout the product, and that can withstand mechanical pressure both in the processing of the capsule and in the chewing of the product in the mouth so that the active ingredients are released in the stomach of the consumer.

BRIEF SUMMARY OF THE INVENTION

Applicant has unexpectedly produced an alternative method for preparing an encapsulated product comprising the steps of:

a) blending an active ingredient with a compressible material to form a compressible mixture;

b) mixing said compressible mixture with a lubricating material to form a tableting mixture;

c) compressing said tableting mixture into a caplet having a diameter from about 1 millimeter to about 7 millimeters and a length from about 1 millimeter to about 7 millimeters.

The present inventive subject matter is also directed to a novel encapsulated product, comprising:

a) at least one active food ingredient;

b) at least one compressible material; and c) at least one lubricating material;

d) wherein said encapsulated product is in the form of a caplet having a diameter of from about 1 millimeter to about 7 millimeters and a length from about 1 millimeter to about 7 millimeters.

An advantage of method of the inventive subject matter is that no heat nor moisture is required for forming the encapsulated product. High levels of active ingredients are obtainable in the products of the inventive subject matter, even though heat or moisture is not required for forming the encapsulated product. In addition, the encapsulated product of the present inventive subject matter has a uniform active ingredient content and may be strong enough to withstand mechanical pressure both in the processing of the product, and in the chewing of the product in the mouth so that the active ingredients are released in the stomach.

DETAILED DESCRIPTION OF THE INVENTION

The encapsulated product of the present invention is a caplet containing a surprisingly high amount of an active ingredient. Applicant has unexpectedly determined that flavors can be entrapped by adsorption and compressed with high load into a small encapsulated product. The void space of the resultant product is very low, particularly when polyols are used as the compressible material, as will be discussed hereinafter.

In a preferred embodiment of the present invention, the encapsulated product of the present inventive subject matter is a caplet shaped like a capsule and having a diameter from about 1 millimeter to about 7 millimeters and a length from about 1 millimeter to about 7 millimeters. Preferably, the diameter of the encapsulated product is about 3 millimeters and the length is about 3 millimeters. The caplets may be coated with a thin surface film to protect the product from moisture or water absorption, from flavor release in the final product system, and from heat and rupture during processing and chewing.

The alternative method of preparing an encapsulated product of the present inventive subject matter contemplates converting liquid active ingredients, including flavors, into small dry caplets or capsules. Powder materials are also available for conversion using the novel method of the inventive subject matter. The novel method is a simple compression process for compacting high levels of active ingredients into a small piece size.

As used herein, the term "active ingredient" includes without limitation: flavors, sweeteners, coloring agents, food additive, spice, herbal ingredients, non-herbal ingredients, medicaments, vitamins, minerals, caffeine, other effervescent agents, and mixtures thereof.

The encapsulated product of the present inventive subject matter contemplates the addition of flavors to confectionery and/or chewing gum products. The flavoring agents which may be used include those flavors known to the skilled artisan, such as natural and artificial flavors. These flavorings may be chosen from synthetic flavor oils and flavoring aromatics and/or oils, oleoresins and extracts derived from plants, leaves, flowers, fruits, and so forth, and combinations thereof. Nonlimiting representative flavor oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Also useful flavorings are artificial, natural and synthetic fruit flavors such as vanilla, and citrus oils including, without limitation, lemon, orange, lime, grapefruit, and fruit essences including apple, pear, peach, grape, strawberry, raspberry, cherry, plum, pineapple, apricot and so forth. These flavoring agents may be used in liquid or solid form and may be used individually or in admixture. Commonly used flavors include mints such as peppermint, menthol, artificial vanilla, cinnamon derivatives, and various fruit flavors, whether employed individually or in admixture.

Other useful flavorings include aldehydes and esters such as cinnamyl acetate, cinnamaldehyde, citral diethylacetal, dihydrocarvyl acetate, eugenyl formate, p-methylamisol, and so forth may be used.

When at least one of the active ingredients of the present inventive encapsulated product is a flavor, the encapsulated product is made according to the following method. If the flavor to be added is liquid, then the liquid flavor is first absorbed onto a solid absorbent. Examples of absorbents on which the liquid may be absorbed include, without limitation, silica gel particles, starches, carbohydrates such as sugars and polyhydroxyalcohols, celluloses, calcium salts such as calcium phosphate, calcium carbonate, and calcium sulfonate, and other absorbing agents in free-flowing powder form. The amount of liquid flavor added depends on the final concentration desired. Generally, though, the liquid flavor will be present in quantities from about 0.1% to 70% by weight of the resultant flavor/absorbent mixture.

The flavor/absorbent mixture is then mixed with a compressible material. Selection of a proper compressible material is dependent on whether the final encapsulated product is to be sugar-free or not. If the encapsulated product is to contain sugar, then the compressible material is, without limitation, a sugar product such "Di-Pac" from the Domino Sugar Corp., a dextrose such as "Cantab" from Compton Knowles Inc., or other compressible sugar materials. If, on the other hand, the encapsulated product is to be sugar-free, then examples of the compressible material are, without limitation, sorbitol, isomalt, maltitol, xylitol, lactitol, calcium phosphates, microcrystalline celluloses, polydextrose, erythritols, other compressible materials and mixtures thereof. Preferably, the compressible material is sorbitol. The flavor/absorbent material is mixed with the compressible material in a dry powder mixer. The amount of compressible material to be added will vary depending on the final encapsulated product. Generally, though, the amount of compressible material added will be such that the flavor will be constitute from about 0.1% to about 70% by weight of the flavor/absorbent/compressible material mixture.

The flavor/absorbent/compressible material mixture is further mixed with a tableting or lubricating material. The lubricating material forms a film around the particles of the material and helps the material flow, compress and eject from the tableting machine. The lubricant or lubricating material may be present in levels up to 5% by weight of the final composition. Examples of usable lubricating materials include, without limitation, fats, emulsifiers, waxes, magnesium stearate, calcium stearate, talc, starches, silicon dioxide, and mixtures thereof. Among the fats, or fatty materials, useful herein include, without limitation, water-insoluble, inert hydrocarbon fats or oils, or their derivatives and mixtures thereof. Such fats or fatty materials include, for example and without limitation, cocoa butter, hydrogenated vegetable tallow, hydrogenated vegetable oils, and derivative mixtures thereof.

Among the emulsifiers useful herein include, without limitation, alkyl aryl sulfonates, alkyl sulfates, sulfonated amides and amines, sulfated and sulfonated esters and ethers, alkyl sulfonates, polyethoxylated esters, mono- and diglycerides, diactyl tartaric esters of monoglyderides, polyglycerol esters, sorbitan esters and ethoxylates, lactylated esters, propylene glycol esters, sucrose esters and mixtures thereof. Among the waxes useful herein include, without limitation, amorphous waxes, anionic emulsifying waxes, bleached waxes, caranda waxes, cetyl esters, cationic emulsifying waxes, microcrystalline waxes, paraffins, refined waxes and mixtures thereof.

The use of particular fats, emulsifiers or waxes may allow the encapsulated product of the present inventive subject matter to provide controlled release of the active ingredient. The controlled release occurs due to the entrapment of the active material in the particular fat, emulsifier or wax.

Furthermore, other additives such as colors, binders, etc. may also be added to this mixture to form the final mixture. The final mixture is then formed into the encapsulated product of the present invention by using a tableting machine. The stations of the tableting machine are set to the desired caplet size, which is from about 1 millimeter to about 7 millimeters diameter and length for the encapsulated.

The flavor content of the final encapsulate product is from about 0.1% to about 70% by weight depending on the absorption system, compression material, and type of flavor. Preferably, the flavor content is from about 1.0% to about 15% by weight when the flavor is initially in liquid form, and from about 10% to about 40% by weight when the flavor is in solid form. Other dry active ingredients could be present in levels approaching 99% by weight depending on the compression granule.

The use of flavor as the active ingredient in the encapsulated product allows for flexibility in adding flavor to food items, confectionery products or chewing gum products. For example, delivery of two or more flavors to a single food item is possible by using encapsulated products containing different flavors in the food item. The delivery of two or more flavors is also possible in confectionery products and chewing gum products.

While the above final step of the method is preferred, other alternate final steps of preparing encapsulated products are contemplated as being within the scope of the inventive subject matter. In particular, the inventive subject matter also contemplates forming larger tablets with the tableting machine, then grinding the larger tablets into smaller pieces. A further final step is forming the sheets of the final product using roller compaction techniques, then grinding the sheets.

Advantages of preparing the inventive encapsulated product in this manner are that no heat and no moisture are needed in this process. Additionally and surprisingly, high concentrations of flavor (as well as other active ingredients) may be incorporated into the final encapsulated product. For example, flavors from about 1% to about 70% of the encapsulated product are possible by using the present inventive subject matter. Furthermore, the encapsulated product of the present inventive subject matter is small enough that when the confectionery or chewing gum product is chewed, the encapsulated product can pass with the saliva and not be disformed by the teeth of the individual chewing.

The present inventive subject matter also contemplates incorporating, without limitation, sweeteners, food additives, spices, herbal ingredients, non-herbal ingredients, vitamins, minerals, and mixtures thereof.

Examples of sweeteners that are available as active ingredients include, without limitation, solid natural or synthetic sweeteners such as amino acid based sweeteners, dipeptide sweeteners, especially aspartame, glycerrhizin, saccharin and its salts, acesulfame salts, cyclamates, steviosides, talin, dihydrochalcone compounds and mixtures thereof. The sweetener is generally present in the encapsulated product from about 0.1% to about 70% by weight of the final encapsulated product. The present inventive subject matter also contemplates having a blend of the above sweeteners as the active ingredient in the encapsulated product. Furthermore, the amount of sweetener contained in one caplet of the encapsulated product may be a dosage equivalent to one teaspoon of sugar. This will allow users of the encapsulated products ease in selecting the number of caplets to be used.

Examples of vitamins that are available as active ingredients include, without limitation, vitamin A (retinol), vitamin D (cholecalciferol), vitamin E group ($\alpha$-tocopherol and other tocopherols), vitamin K group (phylloquinones and menaquinones), thiamine (vitamin $B_1$), riboflavin (vitamin $B_2$), niacin, vitamin $B_6$ group, folic acid, vitamin $B_{12}$ (cobalamins), biotin, vitamin C (ascorbic acid), and mixtures thereof. The amount of vitamin or vitamins present in the final encapsulated product of the present inventive subject matter is dependent on the particular vitamin and is generally the United States' Department of Agriculture Recommended Daily Allowances (USRDA) for that vitamin. For example, if vitamin C is the active ingredient and the encapsulated product is being used in a confectionery or chewing gum targeting adults, the amount of vitamin C in the encapsulated product would be 60 milligrams, which is the USRDA of vitamin C for adults.

Examples of minerals that are available as active ingredients include, without limitation, calcium, magnesium, phosphorus, iron, zinc, iodine, selenium, potassium, copper, manganese, molybdenum and mixtures thereof. As is the case with vitamins, the amount of mineral or minerals present in the final encapsulated product of the present inventive subject matter is dependent on the particular mineral and is generally the USRDA for that mineral. For example, if iodine is the active ingredient and the encapsulated product is being used in a confectionery or chewing gum targeting adults, the amount of iodine in the encapsulated product would be 150 micrograms, which is the USRDA of iodine for adults.

Examples of herbals that are available as active ingredients include, without limitation, echinacea, peppermint, licorice, goldenseal, panax pseudoginseng, grapeseed extract, bilberry, kava, ginko biloba, panax quinquefolium, Siberian ginseng, St. John's wort, bromelian, guglupids, hawthorn, garlic, ginger, angelica species, dandelion, goldenseal, and mixtures thereof. Further, examples of spices that are available as active ingredients include, without limitation, mustard, dillweed, cinnamon, garlic, black pepper, onion, sage, oregano, basil, cream of tartar, targon, cayenne pepper, red pepper, and mixtures thereof. This list of herbals and spices is for exemplary purposes and is not meant to be construed as limiting the inventive subject matter thereto.

It is possible to provide a coating on the encapsulated product. The coating provides protection of the active ingredients from moisture or water absorption. The coating may also allow the release of the active ingredient in the stomach of the individual, and not in the mouth thereof.

The present inventive subject matter also contemplates the use of the encapsulated product in a food item, a confectionery product or a chewing gum product.

As used herein, the term "confectionery" means a product containing a bulking agent selected from a wide variety of materials such as sugar and, in the case of sugarless bulking agents, sugar alcohols such as sorbitol and mannitol. Confectionery material may include exemplary substances as lozenges, tables, toffee, nougat, chewy candy and so forth, In general, the bulking agent will comprise from about 5 to about 99% and preferably 20 to 95% by weight of the activated confectionery product.

Lozenges are forms intended to be sucked and held in the mouth. They may be in the form of various shapes, the most common being flat, circular, octagonal and biconvex forms. The lozenge bases are generally in two forms, hard boiled candy lozenges and compressed tablet lozenges.

The hard boiled candy lozenges are prepared from a mixture of sugar and other carbohydrates that are kept in an amorphous or glassy condition. This form can be considered a solid syrup of sugars generally having form about 0.5 to about 1.5% moisture. Such materials normally contain up to about 92% corn syrup, up to about 70% sugar and form 0.1% to about 5.0% water. The syrup component generally is prepared from corn syrups high in dextrose, by may include other materials. Further active ingredients such as flavoring, sweeteners, vitamins, minerals, and the like may also be added in accordance with the present invention.

Boiled candy lozenges may also be prepared from non-fermentable sugars such as sortitol, mannitol, and hydrogenated corn syrup. A typical hydrogenated corn syrup ois lycasin. The candy lozenges may contain up to about 95% sorbitol, a mixture of sorbitol and mannitol at a ration of about 9.5 to 0.5 up to about 7.5 to 2.5 and hydrogenated corn syrup up to about 55% of the syrup component.

Soft confectionery items include nougat, chewy candy and the like. These materials contain two primary components, namely a high boiling syrup such as corn syrup or the like, and a relatively light texture frappe, generally prepared form gelatin, egg albumen, milk proteins such as casein, and vegetable proteins such as soy protein, and the like. The frappe is generally relatively light, and may, for example, range in density from about 0.5 to about 0.7 g/cc.

The procedure to make soft confectionery items generally involves the formation of a boiled sugar-corn syrup blend to which is added a frappe mixture. The boiled sugar-corn syrup blend may be prepared from sugar and corn syrup blended in parts by weighy ratio of about 90 to 10 to about 10 to 90. This blend is heated to temperatures above 121° C. to remove water and to form a molten mass. The frappe is generally prepared from gelatin, egg albumen, milk proteins such as casein, and vegetable proteins such as soy protein, and the like which are added to a gelatin solution and rapidly mixed at ambient temperature to form an aerated sponge-like mass. The frappe is then added to the molten candy base and mixed until homogenous at temperatures between 65° C. and 121° C.

The encapsulated product of the present invention can then be added as the temperature of the mixture is lowered to about 65–93° C., whereupon additional ingredients may be further added. The soft confectionery formulation is then cooled and formed to pieces of desired dimensions.

As is stated above, the inventive subject matter also includes the incorporation of the encapsulated product into a chewing gum product. As used herein, the term chewing gum means a product containing a chewing gum formulation. In general, the chewing gum formulation will comprise from about 5 to about 99% and preferably 20 to about 95% by weight of the enhanced chewing gum product.

With regard to a chewing gum formulation, such formulations will contain a gum base and various additives, such as sweeteners and flavors which may be supplied by the encapsulated product of the present invention. The gum base employed will vary greatly depending on various factors such as the type of base used, consistency desired and other components to make the final product. In general, amounts of about 5% to about 45% by weight of the final chewing gum composition are acceptable for use in chewing gum compositions with preferred amounts of about 15% to about 25% by weight. The gum base may be any water-soluble gum base well known in the art. Illustrative examples of suitable polymers in gum bases include both natural and synthetic elastomers and rubbers. For example, those polymers which are suitable in gum bases, include, without limitation, substances of vegetable origin such as chicle, jelutong, gutta percha and crown gum. Synthetic elastomers such as butadiene-styrene copolymers, isobutylene-isoprene copolymers, polyethylene, polyisobutyliene and polyvinylacetate and mixtures thereof, are particularly useful.

The gum base component may contain elastomer solvents to aid in softening the elastomer component. Such elastomer solvents may comprise methyl, glycerol and pentaerythritol esters of rosins or modified rosins, such as hydrogenated, dimerized or polymerized rosins or mixtures thereof. Examples of elastomer solvents suitable for use herein include the pentaerythritol ester of partially hydrogenated wood rosin, pentaerythritol ester of wood rosin, glycerol ester of polymerized rosin, glycerol ester of tall oil rosin, glycerol ester of wood rosin and partially dydrogenated wood rosin and partially hydrogenated methyl ester of rosin, such as polymers of alpha-pinene and beta-pinene; terpene resins including polyterpene and mixtures thereof. The solvent may be employed in an amount ranging from about 10% to about 75% and preferably about 45% to about 70% by weight to the gum base.

A variety of traditional ingredients such as plasticizers or softeners such as lanolin, stearic acid, sodium stearate, potassium stearate, glyceryl triacetate, glycerine and the like as well as natural and synthetic waxes, petroleum waxes, such as 35 polyurethane waxes, paraffin waxes and microcrystalline waxes may also be incorporated into the gum base to obtain a variety of desirable textures and consistency properties. These individual additional materials are generally employed in amounts of up to about 30% by weight and preferably in amounts from about 3% to about 20% by weight of the final gum composition.

The chewing gum composition may also include additional fillers such as aluminum hydroxide, alumina, aluminum silicates, calcium carbonate, and talc and combinations thereof. These fillers may also be used in the gum base in various amounts. Preferably the amount of fillers when used will vary from about 4% to about 30% by weight of the final chewing gum composition.

Further, the chewing gum composition will include one or more encapsulated products of the present invention. The encapsulated products of the present invention may provide sweeteners, colorants, and/or flavors to the chewing gum product. The amount of each encapsulated product employed in the chewing gum product will depend on what the encapsulated product is adding to the chewing gum product.

The present inventive subject matter also contemplates the use of the encapsulated product in various other food items, including, without limitation, yogurt, frostings on cakes, nutrition bars, granola bars, candy bars, and the like. The present inventive subject matter also contemplates the use of the encapsulated product in various pharmaceutical applications.

As is stated above, an advantage of method of the inventive subject matter is that no heat nor moisture is required for forming the encapsulated product. In addition, the encapsulated product of the present inventive subject matter has a uniform active ingredient content and may be strong enough to withstand mechanical pressure both in the processing of the product, and in the chewing of the product in the mouth so that the active ingredients are released in the stomach.

The following examples are illustrative of preferred embodiments of the invention and are not to be construed as limiting the invention thereto. All percentages are given in weight percent, unless otherwise noted and equal a total of 100%.

EXAMPLES

Example 1

Preparation of 1% Cherry Flavor Food Enhancement Product

20 grams of liquid cherry flavor was mixed into 20 grams of Syloid 244 and 10 grams of Maltrin M-700. The resultant mixture was further mixed with 1930 grams of DiPac compressible sucrose material. 20 grams of magnesium stearate and 9 grams of red food coloring were then added to the mixture, resulting in 2009 grams of the final mixture. The final mixture was mixed for 3 minutes. The mixture was loaded into a tableting machine.

A series of caplets 3 millimeters in length and 3 millimeters in diameter was produced using 20 KN of force. The punch was then changed in the tableting machine and a series of caplets 1.3 millimeters in length and 1.3 millimeters in diameter was produced using 20 KN of force.

Example 2

Preparation of 1.4% Sugar-Free Peppermint Flavor Encapsulated Product

36 grams of liquid peppermint flavor was mixed with 54 grams of Syloid 244. The resultant mixture was further mixed with 2880 grams of sorbitol. 30 grams of magnesium stearate was then added to the mixture, resulting in 3000 grams of the final mixture. The final mixture was mixed for 3 minutes before the mixture was loaded into a tableting machine. A encapsulated product containing 1.4% peppermint flavor in a 3-millimeter caplet was produced.

Example 3

Preparation of 2.7% Sugar-Free Peppermint Flavor Encapsulated Product

16 grams liquid peppermint flavor was added to 24 grams of Syloid 244. The resultant mixture was further mixed with 1000 grams of the final mixture from Example 2 above. 5 grams of magnesium stearate was then added to the mixture, resulting in 1045 grams of the final mixture. The final mixture was mixed for 3 minutes before the mixture was loaded into a tableting machine. A encapsulated product containing 2.7% peppermint flavor in a 3-millimeter caplet was produced.

Example 4

Preparation of 1% Wintergreen Flavor Food Enhancement Product

20 grams of liquid wintergreen flavor was mixed into 20 grams of Syloid 244 and 10 grams of Maltrin M-700. The resultant mixture was further mixed with 1930 grams of DiPak compressible sucrose material. 20 grams of magnesium stearate was then added, resulting in 2000 grams of the final mixture. The final mixture was mixed for 3 minutes. The mixture was loaded into a tableting machine.

A series of caplets 3 millimeters in length and 3 millimeters in diameter was produced using 20 KN of force. The punch was then changed in the tableting machine and a series of caplets 1.3 millimeters in length and 1.3 millimeters in diameter was produced using 20 KN of force.

Example 5

Preparation of 4.0% Sugar-Free Peppermint Flavor Encapsulated Product

120.00 grams of liquid peppermint flavor was mixed with 180.00 grams of Syloid 244. The resultant mixture was further mixed with 2670.00 grams of sorbitol. 30.00 grams of magnesium stearate was then added to the mixture, resulting in 3000.00 grams of the final mixture. The final mixture was mixed for 3 minutes before the mixture was loaded into a tableting machine. A encapsulated product containing 4.0% peppermint flavor in a 3-millimeter caplet was produced.

Example 6

Preparation of 10% Aspartame Sweetener Encapsulated Product

200 grams of aspartame sweetener was mixed with 20 grams of magnesium stearate. The resultant mixture was further mixed with 1,780 grams of maltitol, resulting in 2000 grams of the final mixture. The final mixture was mixed for 3 minutes before the mixture was loaded into a tableting machine. An encapsulated product containing 10% aspartame in a 3-millimeter caplet was produced.

Example 7

Preparation of 3.0% Folic Acid Encapsulated Product

60 grams of folic acid was mixed with 20 grams of magnesium stearate. The resultant mixture was further mixed with 1920 grams of maltitol, resulting in 2000 grams of the final mixture. The final mixture was mixed for 3 minutes before the mixture was loaded into a tableting machine. An encapsulated product containing 3.0% folic acid in a 3-millimeter caplet was produced.

Example 8

Preparation of 1.0% Sugar-Free Wintergreen Flavor Encapsulated Product

20 grams of liquid wintergreen flavor was mixed with 10 grams of HPMC. The resultant mixture was further mixed with 1950 grams of diabasic calcium phosphate dihydrate. 20 grams of magnesium stearate was then added to the mixture, resulting in 2000 grams of the final mixture. The final mixture was mixed for 3 minutes before the mixture was loaded into a tableting machine. A encapsulated product containing 1.0% wintergreen flavor in a 3-millimeter caplet was produced.

Example 9

Preparation of 1.0% Sugar-Free Wintergreen Flavor Encapsulated Product

20 grams of liquid wintergreen flavor was mixed with 10 grams of HPMC. The resultant mixture was further mixed with 1950 grams of microcrystalline cellulose. 20 grams of magnesium stearate was then added to the mixture, resulting in 2000 grams of the final mixture. The final mixture was mixed for 3 minutes before the mixture was loaded into a tableting machine. A encapsulated product containing 1.0% wintergreen flavor in a 3-millimeter caplet was produced.

Example 10

Preparation of 5.0% Sugared Wintergreen Flavor Encapsulated Product

100 grams of liquid wintergreen flavor was mixed with 150 grams of HPMC. The resultant mixture was further mixed with 1730 grams of Cantab brand dextrose. 20 grams of magnesium stearate was then added to the mixture, resulting in 2000 grams of the final mixture. The final mixture was mixed for 3 minutes before the mixture was loaded into a tableting machine. A encapsulated product containing 5.0% wintergreen flavor in a 3-millimeter caplet was produced.

Example 11

Preparation of 7.5% Sugar-Free Wintergreen Flavor Encapsulated Product 150 grams of liquid wintergreen flavor was mixed with 225 grams of HPMC. The resultant mixture was further mixed with 1605 grams of maltitol. 20 grams of magnesium stearate was then added to the mixture, resulting in 2000 grams of the final mixture. The final mixture was mixed for 3 minutes before the mixture was loaded into a tableting machine. A encapsulated product containing 7.5% wintergreen flavor in a 3-millimeter caplet was produced.

Example 12

Preparation of 7.5% Sugar-Free Wintergreen Flavor Encapsulated Product 150 grams of liquid wintergreen flavor was mixed with 225 grams of HPMC. The resultant mixture was further mixed with 1605 grams of maltitol. 20 grams of magnesium stearate was then added to the mixture, resulting in 2000 grams of the final mixture. The final mixture was mixed for 3 minutes before the mixture was loaded into a tableting machine. A encapsulated product containing 7.5% wintergreen flavor in a 3-millimeter caplet was produced.

Example 13

Preparation of 10% Sugar-Free Wintergreen Flavor Encapsulated Product 200 grams of liquid wintergreen flavor was mixed with 300 grams of HPMC. The resultant mixture was further mixed with 1480 grams of maltitol. 20 grams of magnesium stearate was then added to the mixture, resulting in 2000 grams of the final mixture. The final mixture was mixed for 3 minutes before the mixture was loaded into a tableting machine. A encapsulated product containing 10% wintergreen flavor in a 3-millimeter caplet was produced.

Example 14

Preparation of 10% Sugar-Free Wintergreen Flavor Encapsulated Product 200 grams of liquid wintergreen flavor was mixed with 300 grams of HPMC. The resultant mixture was further mixed with 1480 grams of maltitol. 20 grams of magnesium stearate was then added to the mixture, resulting in 2000 grams of the final mixture. The final mixture was mixed for 3 minutes before the mixture was loaded into a tableting machine. A encapsulated product containing 10% wintergreen flavor in a 3-millimeter caplet was produced.

Example 15

Preparation of 10% Sugared Wintergreen Flavor Encapsulated Product 200 grams of liquid wintergreen flavor was mixed with 300 grams of HPMC. The resultant mixture was further mixed with 1480 grams of Cantab brand dextrose. 20 grams of magnesium stearate was then added to the mixture, resulting in 2000 grams of the final mixture. The final mixture was mixed for 3 minutes before the mixture was loaded into a tableting machine. A encapsulated product containing 10% wintergreen flavor in a 3-millimeter caplet was produced.

Example 16

Preparation of 10% Sugared Wintergreen Flavor Encapsulated Product 200 grams of liquid wintergreen flavor was mixed with 300 grams of HPMC. The resultant mixture was further mixed with 1480 grams of Cantab brand dextrose. 20 grams of magnesium stearate was then added to the mixture, resulting in 2000 grams of the final mixture. The final mixture was mixed for 3 minutes before the mixture was loaded into a tableting machine. A encapsulated product containing 10% wintergreen flavor in a 3-millimeter caplet was produced.

Example 17

Preparation of 50% Aspartame Sweetener Encapsulated Product 1000 grams of aspartame sweetener was mixed with 20 grams of magnesium stearate. The resultant mixture was further mixed with 1000 grams of maltitol, resulting in 2000 grams of the final mixture. The final mixture was mixed for 3 minutes before the mixture was loaded into a tableting machine. An encapsulated product containing 50% aspartame in a 3-millimeter caplet was produced.

Example 18

Preparation of 96.5% Aspartame Sweetener Encapsulated Product 1930 grams of aspartame sweetener was mixed with 20 grams of magnesium stearate. The resultant mixture was further mixed with 50 grams of maltitol, resulting in 2000 grams of the final mixture. The final mixture was mixed for 3 minutes before the mixture was loaded into a tableting machine. An encapsulated product containing 96.5% aspartame in a 3-millimeter caplet was produced.

Example 19

Preparation of 1% Sugar-Free Ginko Biloba Encapsulated Product 20 grams of ginko biloba is mixed with 300 grams of HPMC. The resultant mixture is further mixed with 1660 grams of maltitol. 20 grams of magnesium stearate is then added to the mixture, resulting in 2000 grams of the final mixture. The final mixture is mixed for 3 minutes before the mixture is loaded into a tableting machine. An encapsulated product containing 1% ginko biloba in a 3-millimeter caplet is produced.

Example 20

Preparation of 1% Sugar-Free Siberian Ginseng Encapsulated Product 20 grams of Siberian ginseng is mixed with 300 grams of HPMC. The resultant mixture is further mixed with 1660 grams of maltitol. 20 grams of magnesium stearate is then added to the mixture, resulting in 2000 grams of the final mixture. The final mixture is mixed for 3 minutes before the mixture is loaded into a tableting machine. An encapsulated product containing 1% Siberian ginseng in a 3-millimeter caplet is produced.

The inventive subject matter being thus described, it will be obvious that the same may be varied in many ways. Such variations are not to be regarded as a departure from the spirit and scope of the inventive subject matter, and all such modifications are intended to be included within the scope of the following claims.

What is claimed is:

1. An encapsulated product, consisting essentially of:
    a) at least one active ingredient selected from the group consisting of: flavors, sweeteners, spices, herbal ingredients, vitamins, minerals, and mixtures thereof;
    b) at least one compressible material; and
    c) at least one lubricating material;
    d) wherein said product is in the form of a caplet having a diameter from about 1 millimeter to about 7 millimeters and a length from about 1 millimeter to about 7 millimeters.

2. The encapsulated product of claim 1 wherein said active ingredient is at least one flavor.

3. The encapsulated product of claim 2 wherein said flavor comprises from about 0.1% to about 50% by weight of the final encapsulated product weight.

4. The encapsulated product of claim 3 wherein said flavor comprises from about 1% to about 15% by weight of the final encapsulated product weight.

5. The encapsulated product of claim 1 wherein said active ingredient is a blend of sweeteners.

6. The encapsulated product of claim 1 wherein the active ingredient is a sweetener or a blend of sweeteners in an amount equivalent to one teaspoon of sugar.

7. The encapsulated product of claim 1 further comprising a coating over said caplet, said coating providing protection to said active ingredient.

8. The encapsulated product of claim 1 wherein said compressible material is selected from the group consisting of sugar, polyols, mineral salts, dextrose, sorbitol, isomalt, maltitol, xylitol, lactitol, calcium phosphate, and mixtures thereof.

9. The encapsulated product of claim 8 wherein said compressible material is sorbitol.

10. The encapsulated product of claim 1 wherein said lubricating material is selected from the group consisting of: fats, emulsifiers, waxes, magnesium stearate, calcium stearate, talc, starches, silicon dioxide, and mixtures thereof.

11. The encapsulated product of claim 1 wherein said diameter is about 3 millimeters and said length is about 3 millimeters.

12. The encapsulated product of claim 1 wherein said product provides controlled release of said active ingredient.

13. A method for preparing an encapsulated product, said method consisting essentially of the steps:
    a) blending an active ingredient selected from the group consisting of: flavors, sweeteners, spices, herbal ingredients, vitamins, minerals, and mixtures thereof with a compressible material to form a compressible mixture;
    b) mixing said compressible mixture with a lubricating material to form a final mixture; and
    c) compressing said final mixture into a caplet having a diameter from about 1 millimeter to about 7 millimeters and a length from about 1 millimeter to about 7 millimeters.

14. The method of claim 13 further comprising the step of incorporating said encapsulated product into a confectionery product.

15. The method of claim 13 further comprising the step of incorporating said encapsulated product into a chewing gum product.

16. The method of claim 13 further comprising the step of incorporating said encapsulated product into a pharmaceutical.

17. The method of claim 13 further comprising the step of incorporating said encapsulated product into a food item.

18. The method of claim 13 wherein said compressible material is selected from the group consisting of sugar, polyols, mineral salts, dextrose, sorbitol, isomalt, maltitol, xylitol, lactitol, calcium phosphate, and mixtures thereof.

19. The method of claim 18 wherein said compressible material is sorbitol.

20. The method of claim 13 wherein said lubricating material is selected from the group consisting of: fats, emulsifiers, waxes, magnesium stearate, calcium stearate, talc, starches, silicon dioxide, and mixtures thereof.

21. The method of claim 13 wherein said diameter is about 3 millimeters and said length is about 3 millimeters.

* * * * *